United States Patent
Davies et al.

(10) Patent No.: US 6,203,978 B1
(45) Date of Patent: *Mar. 20, 2001

(54) CAPTURE OF SINGLE STRANDED NUCLEIC ACIDS

(75) Inventors: Martin J. Davies, Kent; Ian James Bruce, East Sussex, both of (GB)

(73) Assignee: du Vergier Ltd., Hoddesdon (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/866,446

(22) Filed: May 30, 1997

Related U.S. Application Data

(60) Provisional application No. 60/018,748, filed on May 31, 1996.

(51) Int. Cl.[7] ............... C12Q 1/68; C12P 19/34; C07H 21/04; C07H 21/02
(52) U.S. Cl. ............ 435/6; 435/91.2; 536/22.1; 536/23.1; 536/24.3
(58) Field of Search ................. 536/24.3, 22.1, 536/23.1; 435/6, 91.2; 935/77.78

(56) References Cited

U.S. PATENT DOCUMENTS

| 5,043,272 | * | 8/1991 | Hartley ............... 435/91.2 |
| 5,512,439 | * | 4/1996 | Hornes et al. ............ 435/6 |
| 5,851,770 | * | 12/1998 | Babon et al. ............ 435/6 |

FOREIGN PATENT DOCUMENTS

| 0 139 489 | * | 5/1985 | (EP) ............ 435/6 |
| 0 192 168 | * | 8/1986 | (EP) ............ 435/6 |

* cited by examiner

*Primary Examiner*—Stephanie Zitomer
(74) *Attorney, Agent, or Firm*—Pearne & Gordon LLP

(57) ABSTRACT

A solid phase substrate derivatized with single stranded nucleic acids having random sequences of nucleotide bases and related method of capturing one or more single stranded nucleic acids by contacting with the solid phase substrate wherein the single stranded nucleic acids anneal to the nucleic acids of the substrate to result in the captured sequences.

13 Claims, 2 Drawing Sheets

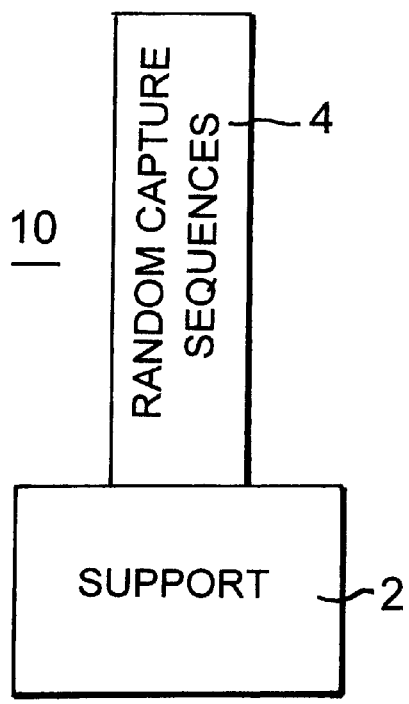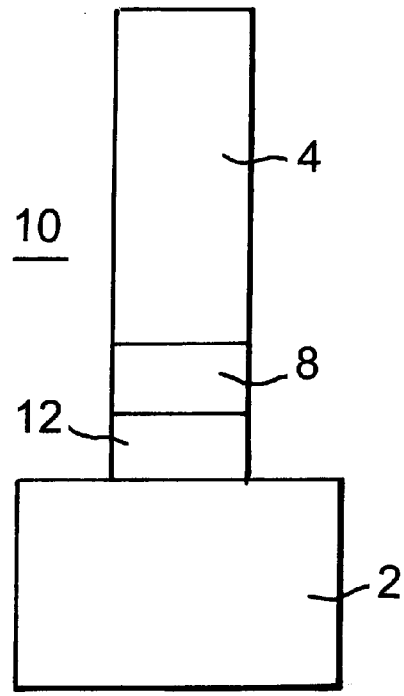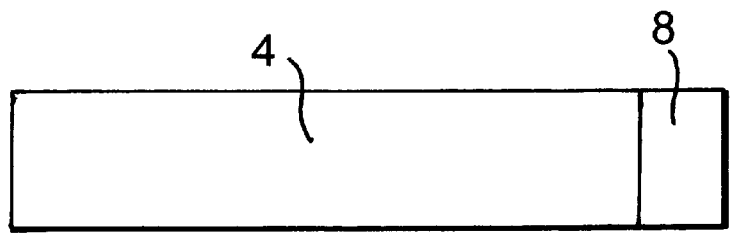

SEQUENCE LISTING

```
(1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: unknown (xi) SEQUENCE DESCRIPTION: SEQ ID NO:1:

GCTCTTAGCA ACGAATACCC TCAAT                                          25

(2) INFORMATION FOR SEQ ID NO:2:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: unknown (xi) SEQUENCE DESCRIPTION: SEQ ID NO:2:

AACAAGTCAC GCCCCAACAC TCTGA                                          25

(2) INFORMATION FOR SEQ ID NO:3:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: unknown
```

```
        (xi) SEQUENCE DESCRIPTION: SEQ ID NO:3:

GCTACAGACA AGGATAAGTT G                                                 21

(2) INFORMATION FOR SEQ ID NO:4:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: unknown (xi) SEQUENCE DESCRIPTION: SEQ ID NO:4:

GTTTTGTATG ACTTTAATTC A                                                 21
```

CAPTURE OF SINGLE STRANDED NUCLEIC ACIDS

CROSS-REFERENCE TO RELATED APPLICATIONS

This application claims priority of provisional U.S. patent application Ser. No. 60/018,748, filed May 31, 1996. The text of the provisional application is incorporated by reference herein.

FIELD OF THE INVENTION

The present invention relates to solid phase supports or substrates for use in the capture of single stranded nucleic acids. The invention also relates to a method of capturing single stranded nucleic acids using such supports or substrates. In particular, but not exclusively, the invention relates to the use of magnetic solid phase supports for capturing PCR (polymerase chain reaction) primers.

BACKGROUND OF THE INVENTION

PCR and other amplification methods offer the best option for sensitive, reliable, cheap and easy detection, characterization, quantitation and discrimination of nucleic acid sequences. A few copies of template target nucleic acid can be replicated in vitro or in situ to provide enough product nucleic acid for analysis. However, the end product often has to be separated and purified from the reaction mixture before its identification and characterization is possible, and whilst amplification can be rapid, identification and characterization can be slow and laborious. The characterization and identification of the nucleic acid amplification product represents a considerable bottleneck in the processing of samples particularly in diagnostic applications of amplification methodologies. For this reason quicker and more convenient methods are desirable for amplification product detection and characterization to improve high throughput screening of biological samples.

With respect to amplification product detection, it is known that PCR products, either modified or unmodified, can be identified and characterized spectrophotometrically. However, determination of the amplification product can be difficult or impossible in the presence of modified or unmodified excess primers present in the reaction mixture at completion of amplification. It is necessary to be able to discriminate between these two species (i.e. amplification products and primers) to permit product detection and characterization, on line, at the end of the amplification process.

In view of the above it is known that single stranded nucleic acid sequences complementary to other nucleic acids can be used to 'capture', by hybridization, such other sequences and that these capture sequences can be derivatized to a support. Such a support (hereinafter known as 'the support') could be a magnetizable or non-magnetizable particle or bead, porous or non-porous membrane, microtitre plate, paper or surface or substrate material that may be contacted with a fluid medium.

Techniques currently exist which make use of these principles. It is possible to detect and characterize a PCR product by its denaturation and subsequent 'capture' to a complementary single stranded oligonucleotide immobilized to a support. The support is frequently represented by a microtitre plate; the single stranded capture sequences are bound to the wall of the wells of the plate and are used to hybridize to a denatured, single stranded amplification product. Excess primers are removed from the system by washing the bound product in the microtitre plate wells, and the amplification product is subsequently detected and characterized by spectrophotometric means. However these techniques are frequently time consuming and complex and risk introducing contamination and artefacts into the process.

An alternative approach would be to remove excess primers from the amplification reaction mixture subsequent to amplification and determine the amplification product directly in solution spectrophotometrically. This would have the benefit of being a potentially faster simpler and more efficient process for amplification product/primer separation and detection and characterization. In the present invention such benefits and advantages over known prior art procedures are provided by a substrate/support where separation, detection and characterization of amplification products are analyzed spectrophotometrically in solution.

Surprisingly we have observed that a magnetizable solid phase support (MSPS) derivatized with single stranded nucleic acids having random sequences of nucleotide bases can anneal to and thereby capture single stranded nucleic acids as effectively as capture sequences having nucleotide sequences complementary to those to be captured. This discovery is applicable to the capture of all single stranded nucleic acid species including PCR primers. Essentially this discovery indicates that complementarity between single stranded nucleic acid capture sequences and the sequence to be captured is unnecessary to effect the latter's capture. We have surprisingly observed that a mixture of totally random sequences, present as oligonucleotides, derivatized to a support can function as well as specific, complementary capture sequences in the removal of single stranded nucleic acids from solution, including primers from PCR reaction mixtures.

SUMMARY OF THE INVENTION

In the present invention, these purposes, as well as others which will be apparent, are achieved generally by providing a solid phase substrate or support derivatized with single stranded nucleic acids having random sequences of nucleotide bases and related method of manufacture. The substrate/support is preferably magnetizable, but any structure capable of attaching the random sequences of nucleotide bases can be used in the invention.

The random sequences of nucleotide bases are prepared by automated synthesis and are preferably 20 to 30 nucleotides long, most preferably 25. However, in accordance with the invention, both shorter and longer sequences also work, for example, random capture sequences as short as 5 nucleotides and as long as 175 nucleotides, which is the upper limit for automated synthesis, can be used. Random sequences longer than 175 bases, made by ligation, can also be used. Prior to attachment to the substrate these sequences are further modified with materials to facilitate addition to the support, such materials include biotin or a primary amine group. The substrate is also modified to promote such addition. To permit conjugation with the biotinylated nucleic acid sequences the support is derivatized with streptavidin. The substrate is also derivatized with carboxymethyl groups which are conjugated to the primary amine group. Both modifications provide means of attachment of the random sequences to the substrate/support which is then used to capture single stranded nucleic acids in amplification processes.

The invention also provides a method of capturing one or more single stranded nucleic acids by addition of the solid phase substrate derivatized with single stranded nucleic acids having random sequences of nucleotide bases to a fluid medium containing both single stranded and double stranded nucleic acids. The single stranded nucleic acids anneal to the nucleic acids of the substrate to result in the captured sequences.

In the embodiment where the substrate is magnetizable, the substrate with the captured sequences is removed by a magnet from the fluid medium to form a medium free of the substrate. This medium is then assayed for the presence of double stranded nucleic acids which have not annealed to the nucleic acids of the substrate.

The captured sequences are single stranded nucleic acids selected from the group consisting of oligonucleotides, polynucleotides and nucleic acid bases. Preferably, the captured sequences are primers, particularly polymerase chain reaction primers, used in nucleic acid amplification reactions.

In addition the primers and their amplification products produced can be made fluorescent by attaching a label to the 5'-terminus of the primer or attached to a nucleotide base of the primer. The labels used in the invention process include fluorochrome or a primary amine group and are preferably in the form of its N-hydroxysuccinimide ester or its isothiocynate derivative.

Encompassing the various aspects of the invention a method for assaying double stranded nucleic acids is provided. The process includes treatment of a fluid medium containing single and double stranded nucleic acids with the magnetizable solid phase substrate derivatized with single stranded nucleic acids having random sequences of nucleotide bases causing the single stranded nucleic acids to anneal to the nucleic acids of the substrate to result in the captured sequences. The captured sequences are removed with a magnet to form a medium free of substrate and assaying the medium for the presence of double stranded nucleic acids which have not annealed to the nucleic acids of said substrate.

Other objects, features and advantages of the present invention will be apparent when the detailed description of the preferred embodiments of the invention are considered in conjunction with the drawings, which should be construed in an illustrative and not limiting sense as follows:

BRIEF DESCRIPTION OF THE DRAWINGS

FIG. 1 is a graphic illustration of the solid phase substrate of the invention showing attachment of the random capture sequence to the support;

FIG. 2A is a graphic illustration of the attachment of the random capture sequences to the substrate, where the support is derivatized with materials 12, such as streptavidin or carboxymethyl groups, to attach the random sequences;

FIG. 2B represents the modification of the random capture sequence with a function 8, such as biotin or a primary amine group, for attachment to the support;

DETAILED DESCRIPTION OF THE INVENTION

As used throughout the specification the terms substrate and support are used interchangeably and are meant to refer to the same feature of the invention. Both the substrate and support provide the structure for attachment of the random sequences of nucleotide bases.

In accordance with a first aspect of the invention and as illustrated in FIG. 1, there is provided a solid phase support or substrate 2 derivatized with single stranded nucleic acids having random sequences of nucleotide bases 4.

The random sequences of nucleotide bases 4 derivatized to the support 2 may be referred to as 'random capture sequences' and are attached to the support at their 5' or 3'-terminus, or at one or more of the nucleotide bases of the single stranded nucleotides. Preferably, the random capture sequences are attached to the support at their 5'-terminus. It is to be understood that the single stranded nucleic acids may be composed partially or entirely of random sequences of nucleotides.

Figure 3A:
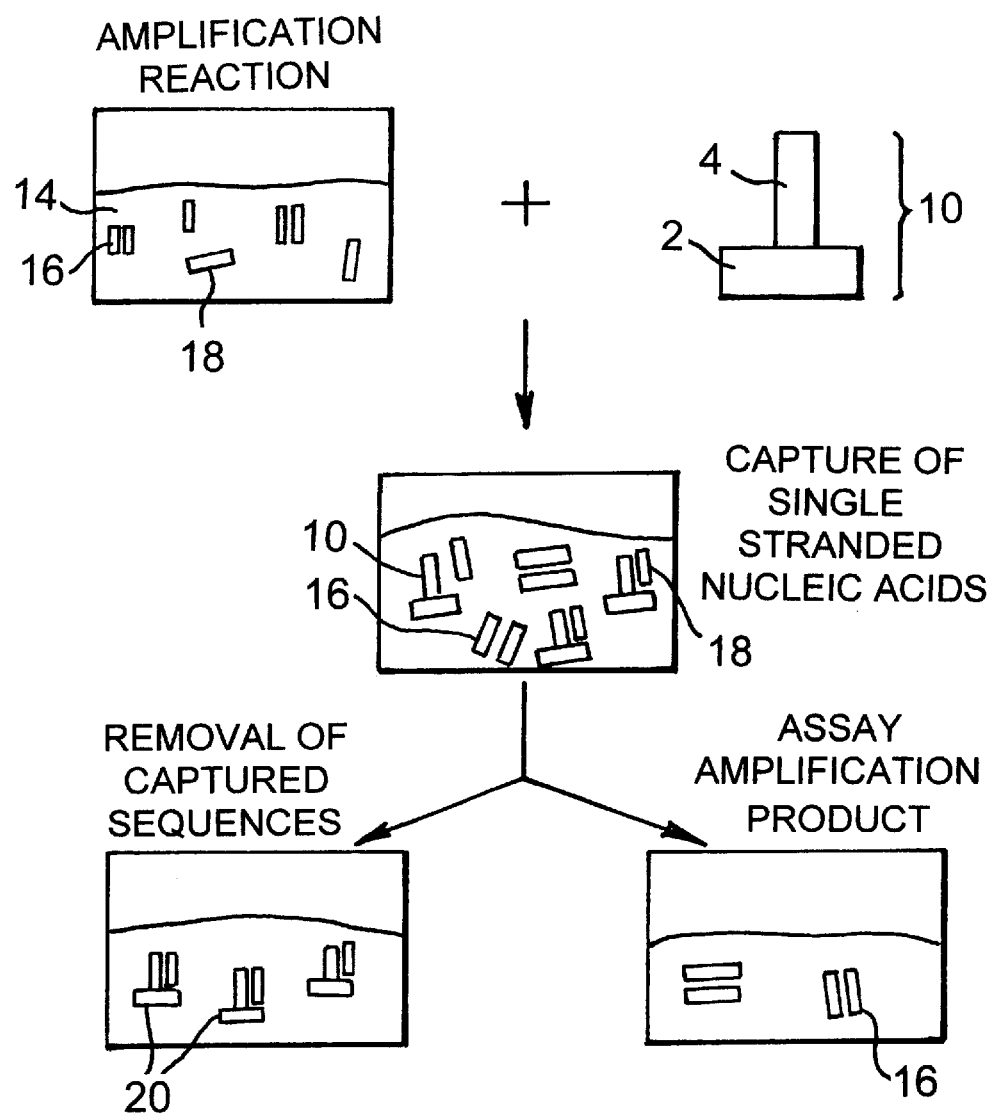
FIG. 3A is a schematic representation of the invention process of capturing single stranded nucleic acids.

In accordance with a second aspect of the invention and as illustrated in FIG. 3A, there is provided a method of capturing one or more single stranded nucleic acids 18, comprising contacting a fluid medium 14 containing such nucleic acids with a support derivatized with single stranded nucleic acids having random sequences of nucleotide bases 10 whereby the one or more single stranded nucleic acids anneal to the nucleic acids with which the solid phase support is derivatized 20.

The one or more single stranded nucleic acids to be captured may be oligonucleotides, polynucleotides or longer 18. Especially, the single stranded nucleic acids may be primers used in nucleic acid amplification reactions, such as PCR primers.

The solid phase support 2 may be a magnetizable solid phase support (MSPS) which by means of a magnet may be removed from the medium or concentrated and immobilized in a portion of the medium leaving the remainder of the medium free of the support, to enable the medium or the remainder of the medium to be assayed (e.g. by spectrophotometric means) for the presence of nucleic acids which have not annealed to the nucleic acid with which the support has been derivatized. In this way, when PCR has been effected, the amplification product 16 can be left in solution and is assayable by spectrophotometric means.

In addition, this method can be further modified by labeling the primers used in the amplification reaction at their 5'-terminus thereby making them and their products fluorescent. This embodiment is described and illustrated in Examples 2 through 4 herein. Alternatively, the primers may also be labeled at one of their nucleotide bases.

The random capture sequences for derivatizing the support may be prepared by automated synthesis, according to procedures as known in the art, and can be from 5 to over 175 nucleotides long. Preferably the random sequences are between 20 to 30 nucleotides long, most preferably about 25. Although the upper limit for automated synthesis is 175 bases, longer sequences can be obtained by ligation.

In the preparation of random capture sequences, as illustrated in FIG. 2B, a function that enables the sequence to be attached to the solid phase support is also required to be present on the sequence. For example, the function may be biotin or a primary amine group. The function may be introduced at the 5'-terminus or the 3'-terminus of the random capture sequences or it may be introduced at one or more of the nucleotide bases of the random capture sequences. In particular, it may be introduced at the 5'-terminus.

As illustrated in FIG. 2A, the support may be derivatized with the random capture sequences by being conjugated thereto in accordance with standard procedures 12. For example the support may be derivatized with streptavidin 12 to permit conjugation with biotinylated random capture sequences. Alternatively, the support may be derivatized with carboxymethyl groups 12 according to standard procedures, and the carboxymethyl groups can be conjugated to random capture sequences possessing a primary amine group at the 5'-terminus, using known methods.

The primers used in the amplification reactions may also be prepared by automated synthesis, according to procedures as known in the art.

Figure 3B:
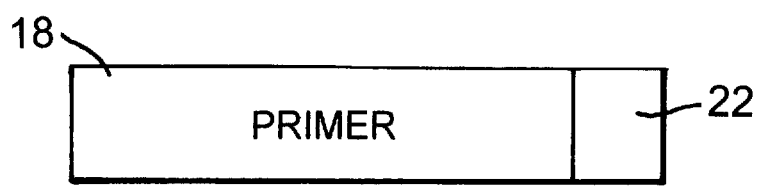
FIG. 3B represents the modification of the primer sequence with a label, such as a fluorochrome or primary amine.

As illustrated in FIG. 3B, if a label 22, or a function to which a label can be attached, is introduced at the 5'-terminus of the primer 18 during automated synthesis, then this can improve the opportunity for subsequent spectrophotometric detection of the amplification product. The label or function introduced at the 5'-terminus may be, or example, a fluorochrome or biotin. Alternatively, the label may be introduced at one of the nucleotide bases of the primer.

The function to which a label may be attached at the 5'-terminus of a synthetic oligonucleotide (primer) is commonly a primary amine group. A label such as that referred to above may be attached to this primary amine group and should be ideally in the form of its N-hydroxysuccinimide (NHS) ester or isothiocyanate (ITC) derivative, which can be attached using known methods.

The following examples illustrate the invention. Example 1 describes the preparation of solid phase substrates for use in the capture of single stranded nucleic acids. Example 2 describes primer solutions treated with substrates of Example 1 having random capture sequences compared with treatment with specific capture sequences complementary to the primer sequences. Examples 3 and 4 illustrate use of the invention substrates in PCR amplification reactions. These examples are merely representative and are not inclusive of all the possible embodiments of the invention.

EXAMPLE 1

Solid phase supports, in accordance with the invention, for use in the capture of single stranded nucleic acids were prepared. Random capture sequences 25 bases in length were synthesized by 24 consecutive additions of mixed AGCT phosphoramidites to a mixed AGCT column, prepared by mixing equal amounts of controlled pore glass (CPG) support from individual columns of CPG-A, CPG-C, CPG-T and CPG-G and repacking in a column assembly.

Although the random sequences prepared in accordance with this example are 25 bases in length, these sequences are only representative, not limiting, to the invention. The random capture sequences of the invention are from 5 to over 175 nucleotides long. Preferably 20 to 30, most preferably 25.

The sequences of the invention are totally random. They are undefined and unknown. They are prepared in accordance with the protocol above by automated synthesis, as known in the art. Specifically, the random sequences are prepared by consecutive additions of equal volume aliquots from a single vessel containing a mixture of A, G, C and T phosphoramidites (supplied by Perkin Elmer Labs, Foster City, Calif.), which are mixed in proportions that ensure equal reactivity of each, such that there is an equal chance of each A, G, C or T phosphoramidite becoming attached to the terminus of the sequence as it is synthesized.

The 3'-terminus CPG (controlled pore glass) support is prepared by mixing A-CPG, G-CPG, T-CPG and C-CPG taken from individual columns, in equal amounts, in a single column assembly, and carrying out the subsequent consecutive additions of mixed A/G/C/T phosphoramidites to this. The total number of possible sequences that can be prepared, according to the example, is $4^{25}/2$.

"Specific" capture sequences complementary to the forward and reverse primer sequences given in Examples 2 to 4 below, were similarly synthesized but using a selected A, G, C or T phosphoramidite in each addition. All capture sequences were prepared with a 5'-biotinylated terminus introduced at the final step of the automated synthesis.

5'-biotinylated capture sequences of 25 nucleotide bases' length were bound to streptavidin-coated paramagnetic beads (Dynal Ltd, Wirral, United Kingdom) in high salt buffer (1M NaCl, 10 mM tris.HCL, 1 mM EDTA, pH8) according to the manufacturer's protocol. The resulting supports were stored in sterile distilled water at a concentration of 10 mg ml$^{-1}$, at 4° C. These supports, unless otherwise indicated, were used in the Examples below.

EXAMPLE 2

Primer sequence solutions were treated with the invention supports having random capture sequences as prepared in Example 1 and were also treated with "specific" capture sequences complementary to the forward and reverse primer sequences. The following protocol was followed.

Two 50 μl aliquots of a solution containing 0.2 μM each of the Eco RY13 forward and reverse primers listed below (Sequence ID Nos. 1 and 2), which were labelled at their 5'-terminus with rhodamine, were diluted with 50 μl of 20×SSPE buffer (2.98M NaCl/0.23 NaH$_2$PO$_4$/0.02M EDTA)and added to 0.5 mg and 1.0 mg, respectively, of support (predrained) derivatized with random capture sequences as described in Example 1. The Eco RY13 forward and reverse primers are well known in the art.

*Escherichia coli* RY13 Primer Sequences

5'-GCTCTTAGCAACGAATACCCTCAAT 3' (forward); SEQ. ID No. 1

5'-AACAAGTCACGCCCCAACACTCTGA-3' (reverse); SEQ. ID No. 2

A ligand loading of 200 pmol of primer per milligram of support was used. This amount represents the amount of derivatized group present on the support. Each suspension was mixed gently at 22° C. for periods up to 10 min, the support was immobilized using a magnet, the supernatants from each removed, and its fluorescence determined.

As a comparison, a further 50 μl aliquot of the same primer solution was taken and diluted with 50 μl of 20×SSPE buffer, and added to 0.5 mg of supports derivatized with specific capture sequences complementary to the Eco RY13 primer sequences. The suspension was mixed, and the supernatant removed and analyzed as before.

All fluorescence measurements were performed using a Jenway 6200 fluorimeter (Jenway Ltd. Dunmow, United Kingdom) in a 45 μl quartz fluorimetry cuvette (Helma Ltd, Westcliffe-on-Sea, United Kingdom). The fluorescence of the stock primer solution before primer removal was scaled to 100 arbitrary fluorescence units; a blank reading scaled to zero was taken using 1:1 water:20×SSPE. An excitation wavelength of 546 nm and emission detection wavelength of 589 nm were used.

TABLE I

| Capture supports/mg | Incubation Time (min) | | |
|---|---|---|---|
| (Type of capture sequence) | 2 | 5 | 10 |
| | Fluorescence | | |
| 0.5 (specific) | 18 | 16 | 16 |
| 0.5 (random) | 41 | 37 | 33 |
| 1.0 (random) | 30 | 20 | 16 |

TABLE I illustrates the fluorescence remaining after capture of 5'-rhodamine labelled EcoRl primers by specific and random sequences immobilized to paramagnetic supports. The support with captured sequences were removed by magnets with the remaining supernatant being analyzed. Readings are in arbitrary fluorescence units. Stock solution of primers was scaled to 100 units. These represent average results from 3 identical experiments.

As shown in TABLE I, it is seen that 1 mg of random sequence capture supports removes practically as much labelled primer from solution as does 0.5 mg of specific, complementary sequence supports. 0.5 mg of random sequence supports captures less labelled primer that 0.5 mg of specific, complementary supports.

It should be noted that in a control experiment where the labelled primers were incubated with Dynal beads not derivatized with oligonucleotide capture sequences, the amount of fluorescently labelled primer removed was less that 5% of the total initially present.

EXAMPLE 3

This example illustrates the use of the invention substrates in a PCR amplification reaction.

A PCR amplification of a 680 base-pair region of the DNA sequence encoding the restriction enzyme EcoRl (the sequence of which is well-known in the art) was performed using the Eco RY13 primers (Sequence ID Nos. 1 and 2) listed in Example 2, using the following protocol.

PCR reaction mixtures contained reaction buffer (10 mM Tris-HCl, 1.5 mM magnesium chloride, 50 mM KCl, pH 8.3), 200 µM (each) deoxynucleotide triphosphates, 0.2 µM each primer, 2 units Taq DNA polymerase (Boehringer Mannheim Limited), 100 ng template DNA and deionized water to a final volume of 100 µl.

PCR amplification was performed using a Techne PHC-3 Thermal Cycler (Techne (Cambridge) Limited, Duxford, United Kingdom) using the following conditions: initial heat denaturation at 94° C. for 5 min and annealing for 1 mm at 55° C. and then 30 cycles of heat denaturation at 94° C. for 1 min, primer annealing at 55° C. for 1 min and DNA extension at 72° C. for 1 min. A final extension at 72° C. for 5 min was also performed. Both primers were labelled at their 5'-terminus with rhodamine.

Two 50 µl aliquots of the PCR amplification mixture were taken, diluted with 20×SSPE, and incubated as described in Example 2 with 0.5 mg, and 1.0 mg, respectively, of random sequence capture supports, and 0.5 mg of specific, complementary sequence capture supports. The fluorescence remaining in the supernatants was determined as before in Example 2 and summarized below in TABLE II.

TABLE II

| Support/mg (Type of capture sequence) | Incubation time/min | Fluorescence remaining after incubation with beads |
|---|---|---|
| 0.5 (specific) | 5 | 44 |
| 0.5 (random) | 5 | 79 |
| 1.0 (random) | 10 | 45 |

TABLE II illustrates the comparison of capture of 5'-rhodamine labelled EcoRl primers from PCR mixtures by specific and random sequences immobilized to paramagnetic supports, following amplification of EcoRl restriction enzyme sequence. The support with captured sequences were removed by magnets with the remaining supernatant being analyzed. Amplification mixture was scaled to 100 arbitrary fluorescence units. These figures represent average results from 3 identical experiments.

As shown in TABLE II, it is seen that 1 mg of random sequence supports removes as much fluorescent primer from solution as does 0.5 mg of specific, complementary sequence supports.

The remaining supernatants were analyzed by agarose gel electrophoresis. Although fluorescently labelled primers were used in the amplification process, no bands due to fluorescent primers were observed in the supernatant remaining after incubation with the random sequence supports by UV transillumination and auto fluorescence, or by ethidium bromide staining followed by UV transillumination.

EXAMPLE 4

This example illustrates the use of the invention substrates in a PCR amplification reaction.

A PCR amplification of 659 base-pair sequence of the coding region of the *Legionella pneumophila* macrophage infectivity potentiator (mip) gene was performed, using the primers listed below (Sequence ID Nos. 3 and 4), which were labelled at their 5'-terminus with rhodamine. Sequence ID No. 3 represents *Legionella pneumophila* upper (forward) primer and Sequence ID No. 4 represents *Legionella pneumophila* lower (reverse) primer. The sequences of this gene and primers are well known in the art.

*Legionella pneumophila* Primer Sequences

LPU: 5'-GCTACAGACAAGGATAAGTTG-3'; SEQ. ID No. 3

LPL: 5'-GTTTTGTATGACTTTAATTCA-3'; SEQ. ID No. 4

Amplification was performed according to the protocol as set forth in Example 3. Capture of excess primers was carried out using random sequence capture supports according to Example 2, except a ligand loading of 40 pmol of oligonucleotide per milligram of support was used, and incubation was for 30 min at 65° C.

Fluorimetric analysis was performed as described in preceding Examples 2 and 3.

PCR products and excess primers were also separated and recovered for assay from agarose gels. 20 $\mu$l of a PCR mixture after thermal cycling was loaded into a well of 1.5% low melting temperature agarose gel (NuSieve GTG Agarose, FMC BioProducts, United States of America) and electrophoresed in TBE buffer (0.089M Trise.HCL 0.089M boric acid, 0.002M EDTA, pH 8.0) at 7Vcm$^{-1}$ for 2 hours. Gels were subsequently visualized on a UV transilluminator and fluorescent product and primer bands excised using a sterile scalpel blade. The product/primer gel slice (approximately 50 μl) was diluted with 300 μl of sterile distilled water and dissolved by heating.

TABLE III below summarizes the fluorimetric analysis and illustrates the comparison of separation of 5'-rhodamine labelled L. Pneumophila primers from PCR mixtures by random sequence capture paramagnetic supports and agarose gel electrophoresis, following amplification of 659 bp sequence of the mip gene. The amplification mixture was scaled to 100 arbitrary fluorescence units. These figures represent average results from 3 identical experiments.

TABLE III

| Method of Separation | Fluorescence due to product | Fluorescence due to primers |
|---|---|---|
| Random sequence magnetic capture support | 26 | 74 |
| Agarose gel electrophoresis | 27 | 59 |

With reference to TABLE III it is seen that the values obtained for fluorescence generated by the PCR product alone are in close accord with that which was observed to be left in solution after incubation with the random capture supports, which implies that the fluorescence remaining in solution is entirely due to double stranded PCR product. This is also confirmed by the elution and fluorescence analysis of the excess primer band which gave a fluorescence value equal to 100 arbitrary fluorescence units minus that of the product fluorescence.

The invention now being fully described, it will be apparent to one of ordinary skill in the art that many changes and modifications can be made thereto without departing from the spirit or scope of the invention as set forth herein.

What is claimed is:

1. A method of assaying labeled double stranded amplification products in a fluid medium expected to further contain labeled single stranded nucleic acids including primers, wherein the amplification product labels and the single stranded nucleic acid labels are the same, comprising:

(a) contacting the fluid medium with a solid phase substrate derivatized with single stranded nucleic acids having random sequences;

(b) capturing the labeled single stranded nucleic acids by hybridizing to the random sequence nucleic acids on the solid phase substrate;

(c) removing the solid phase substrate with the captured labeled single stranded nucleic acids;

(d) assaying the label remaining in the fluid medium to thereby assay the labeled double stranded amplification products.

2. The method according to claim 1, wherein said solid phase substrate is magnetizable and is removed by a magnet.

3. The method according to claim 1, wherein said captured single stranded nucleic acids are selected from the group consisting of oligonucleotides and polynucleotides.

4. The method according to claim 1, wherein said primers are polymerase chain reaction primers.

5. The method according to claim 1, wherein the label is provided by 5' modification of the double stranded amplification products and primers or by introduction of the label at one of the nucleotides of the primers.

6. The method according to claim 1, wherein said single stranded nucleic acids having random sequences of nucleotides are prepared by automated synthesis.

7. The method according to claim 1, wherein the label is a fluorochrome attached to the 5' terminus of the primer or to one of the internal nucleotides of the primer, and the amplification products are assayed by spectrophotometrically detecting the label.

8. The method according to claim 7, wherein said label is attached by means of a linking group constituted by a primary amine group.

9. The method according to claim 7, wherein said label is attached by means of a linking group constituted by an N-hydroxysuccinimide ester or its isothiocyanate derivative.

10. The method according to claim 1, wherein the solid phase substrate derivatized with random sequence single stranded nucleic acids is prepared by the steps of:

(i) adding biotin to the 5' or 3' terminus or to one or more of the internal nucleotides of said random sequence nucleic acids;

(ii) derivatizing the solid phase substrate with streptavidin;

(iii) conjugating the biotinylated random sequence nucleic acids to the streptavidin whereby the random sequence nucleic acids are attached to the substrate.

11. The method according to claim 1, wherein the solid phase substrate derivatized with random sequence single stranded nucleic acids is prepared by the steps of:

(i) adding a primary amine group to the 5' or 3' terminus or to one or more of the internal nucleotides of said random sequence nucleic acids;

(ii) derivatizing the solid phase substrate with carboxymethyl groups; and (iii) conjugating the primary amine groups to the carboxymethyl groups whereby the random sequence nucleic acids are attached to the substrate.

12. The method according to claim 5, wherein said label is attached by means of a linking group constituted by a primary amine group.

13. The method according to claim 5, wherein said label is attached by means of a linking group constituted by an N-hydroxysuccinimide ester or its isothiocyanate derivative.

* * * * *